United States Patent [19]

Azuma et al.

[11] Patent Number: 5,252,588

[45] Date of Patent: Oct. 12, 1993

[54] PERCUTANEOUSLY ABSORBABLE CROSSLINKED POLYVINYLPYRROLIDONE EPERISONE OR TOLPERISONE PREPARATION

[75] Inventors: Masato Azuma; Tsutomu Negama, both of Osaka; Mitsuhiro Yoshida; Hiroyuki Fujimori, both of Saitama, all of Japan

[73] Assignees: Sekisui Kagaku Kogyo Kabushiki Kaisha, Osaka; Sansho Co., Ltd.; Eisai Co., Ltd., both of Tokyo, all of Japan

[21] Appl. No.: 13,018

[22] Filed: Feb. 2, 1993

Related U.S. Application Data

[63] Continuation of Ser. No. 683,281, Apr. 10, 1991, abandoned.

[30] Foreign Application Priority Data

Apr. 27, 1990 [JP] Japan ................... 2-112792

[51] Int. Cl.$^5$ .................. A61K 31/445; A61K 9/70
[52] U.S. Cl. .................... 514/317; 424/449; 514/946; 514/947
[58] Field of Search .......... 514/317, 788, 946, 947; 424/449

[56]       References Cited
       U.S. PATENT DOCUMENTS

| 3,995,047 | 11/1976 | Morita et al. | 514/317 |
| 4,695,465 | 9/1987 | Kigasawa et al. | 424/449 |
| 4,830,851 | 5/1989 | Tracy et al. | 424/78 |
| 4,837,026 | 6/1989 | Rajakhyaksha | 424/449 |
| 4,879,275 | 11/1989 | Minaskanian et al. | 514/24 |
| 5,032,402 | 7/1991 | Digenis et al. | 424/448 |
| 5,059,427 | 10/1991 | Yoshida et al. | 424/449 |
| 5,073,375 | 12/1991 | Yoshida et al. | 424/449 |

FOREIGN PATENT DOCUMENTS 0181970 5/1986 European Pat. Off. .
0295411 12/1988 European Pat. Off. .

OTHER PUBLICATIONS

CA:105(10):85214g-Fukuda.
CA:108(19):167333w-Tsuji.
Merck Index; Eleventh Edition, pp. 7700-7701 #7700 (1989).
Patent Abstracts of Japan, vol. 9, No. 66 (C-271) [1789], Mar. 26, 1985, Japan 59-199628.

*Primary Examiner*—Frederick E. Waddell
*Assistant Examiner*—T. J. Criares
*Attorney, Agent, or Firm*—Flynn, Thiel, Boutell & Tanis

[57] ABSTRACT

A pharmacological composition for percutaneous administration to a human patient comprises a pharmacologically effective amount of eperisone, a salt thereof, tolperisone or a salt thereof, a water-swellable crosslinked polyvinylpyrrolidone and a base carrier, and exhibits improved percutaneous absorption.

8 Claims, 2 Drawing Sheets

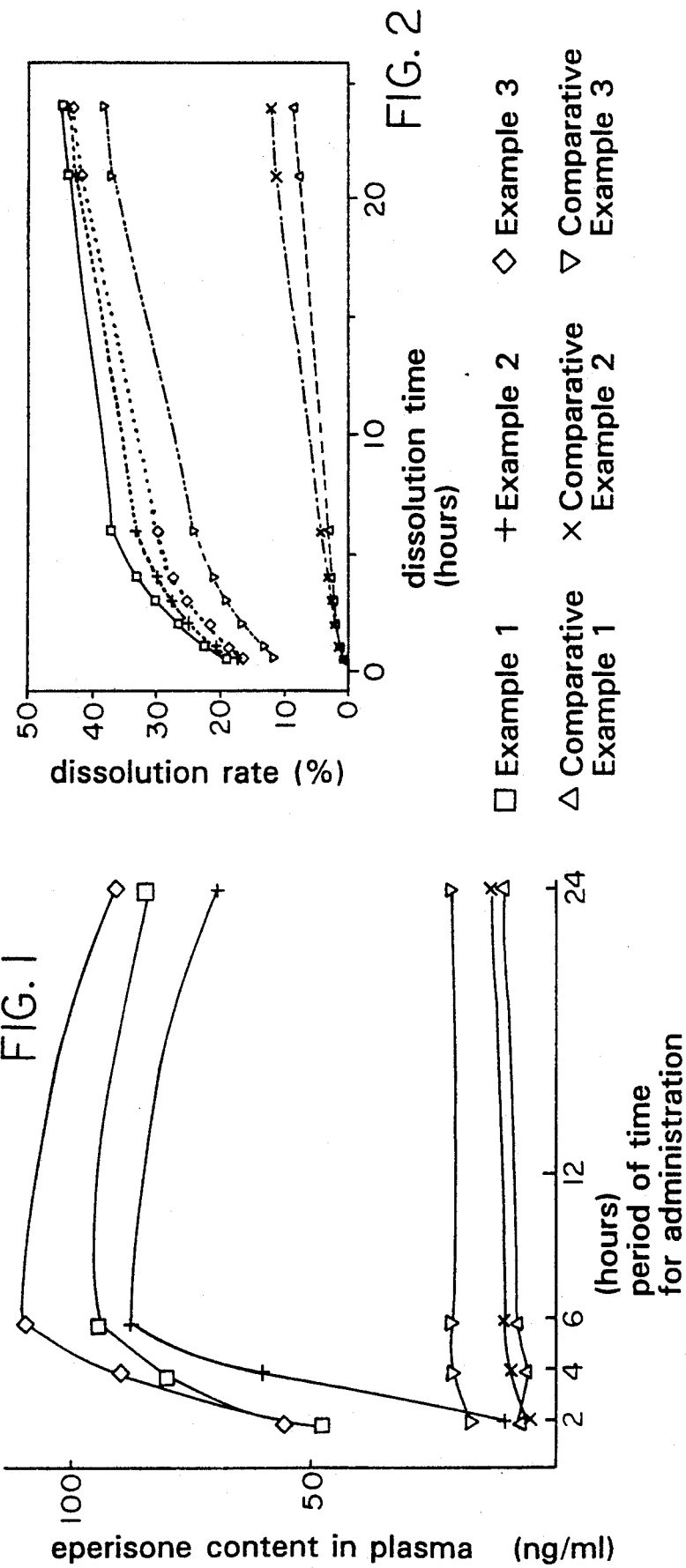

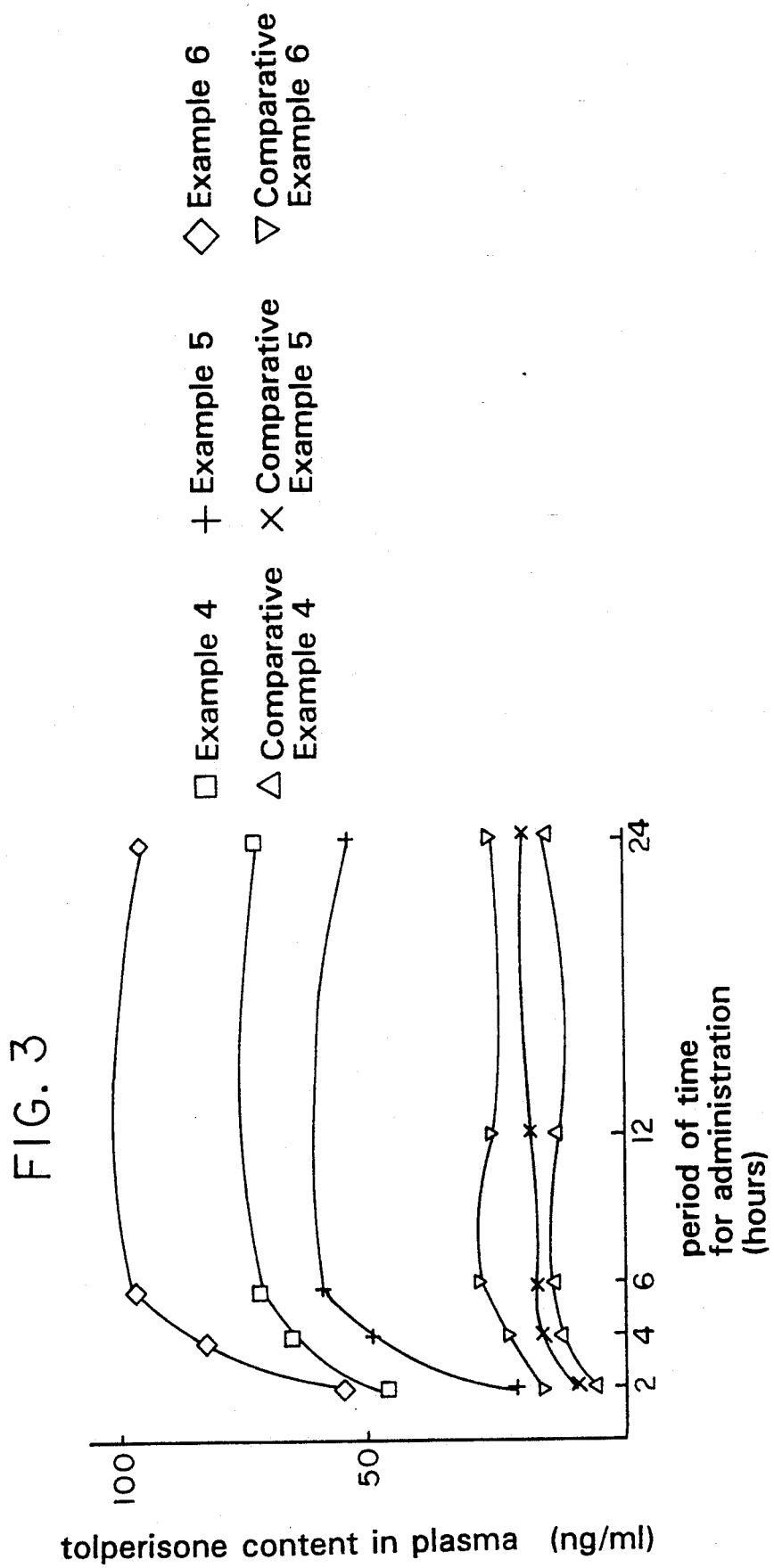

PERCUTANEOUSLY ABSORBABLE CROSSLINKED POLYVINYLPYRROLIDONE EPERISONE OR TOLPERISONE PREPARATION

This application is a continuation of U.S. Ser. No. 07/683,281, filed Apr. 10, 1991, now abandoned.

FIELD OF INDUSTRIAL APPLICATION

The present invention relates to a percutaneously absorbable preparation for the percutaneous administration of eperisone, tolperisone or a salt thereof. Particularly, the present invention relates to a pharmaceutical preparation of eperisone, tolperisone or a salt thereof which has excellent percutaneous absorbability.

PRIOR ART

Eperisone, tolperisone and salts thereof (hereinafter referred to generically as the "invention compound") have been used as remedies for syndromes due to spastic paralysis or paramyotonia due to diseases such as cervicobrachial syndrome, periarthritis of shoulder and lumbago. Generally, the invention compounds are orally administered. When a drug is orally administered, however, the drug absorbed by the intestines is decomposed by metabolism in the liver at a considerably high ratio before it exhibits a pharmacological effect at an affected part. Since a considerable amount of a drug is absorbed within a short duration in time, an adverse reaction may be liable to occur.

Meanwhile, it has been practiced to make a drug (physiologically active substance) absorb through the skin in the form of a percutaneously absorbable preparation. Percutaneous administration has various advantages. That is, a percutaneously absorbed drug can reach an affected part without being decomposed by metabolism in the liver. Further, percutaneous administration hardly causes gastrointestinal disorders which may likely be caused by oral administration. An adverse reaction due to the absorption of a large amount of a drug within a short duration can be reduced by releasing a drug in a rate controlled manner by percutaneous administration. The frequency of administration of a drug can be reduced by keeping the release rate thereof constant for a long period of time.

In the percutaneous administration of a drug, however, it is hard to make the drug absorbable in a sufficient amount in many cases since the permeability of the drug through the skin is poor in general. The corneal layer of the epidermis acts as a barrier against the invasion of foreign substances into the body, so that a satisfactory amount of a drug to exert its pharmacological action cannot be absorbed through the skin. Percutaneous absorbability is improved by the addition of an enhancer for absorbability which can lower the barrier function of the corneal layer.

For example, Japanese Patent Laid-Open No. 52716/1989 discloses a percutaneously absorbable preparation which is improved in the percutaneous absorbability of the invention compound by the addition of a monoglyceride of a fatty acid having 8 to 12 carbon atoms and/or a lactate of a fatty alcohol having 12 to 18 carbon atoms as a percutaneous absorption accelerator. However, the percutaneously absorbable preparation thus prepared is still insufficient in the percutaneous absorbability of the invention compound. Particularly, a pharmaceutical preparation of an adhering type containing such a percutaneous absorption enhancer is still unsatisfactory in the practical use.

SUMMARY OF THE INVENTION

In the invention, an enhancer or accelerator for percutaneous absorption is proposed in combination with the specified pharmacologically active compound.

The present invention aims at solving the above problems of the prior art and an object thereof is to provide a percutaneously absorbable preparation which permits an effective percutaneous administration of eperisone, tolperisone or a salt thereof.

The present invention relates to a percutaneously absorbable preparation comprising eperisone, tolperisone or a salt thereof, a crosslinked polyvinylpyrrolidone and a base, wherein said crosslinked polyvinylpyrrolidone is water-swellable. The above object can be attained by taking this preparation.

The invention provides a pharmacological composition for percutaneous administration to a human patient, which comprises a pharmacologically effective amount of eperisone, a salt thereof, tolperisone or a salt thereof, a water-swellable crosslinked polyvinylpyrrolidone and a base carrier, having improved percutaneous absorption.

It is preferable that the composition or preparation comprises 0.05 to 30 percent by weight of eperisone, a salt thereof, tolperisone or a salt thereof, 0.5 to 20 percent by weight of the water-swellable crosslinked polyvinylpyrrolidone and a base carrier. It may further comprise up to 10 percent by weight of of a percutaneous absorption enhancer.

It is preferable that the polyvinylpyrrolidone is a copolymer of N-vinyl-2-pyrorrolidone and 0.1 to 20 percent by weight, based on the N-vinyl-2-pyrorrolidone, of a polyfunctional monomer.

It is preferable that eperisone, a salt thereof, tolperisone and a salt thereof are contained in an amount of not less than their respective saturated solubility and they are dispersed in the form of microcrystals in the base.

According to a preferable embodiment of the present invention, eperisone, tolperisone or a salt thereof is contained in a base in an amount exceeding its solubility and is dispersed therein in a microcrystalline state.

The invention compound used as an active ingredient in the present invention includes eperisone, tolperisone and salts thereof. The salts include chlorides, phosphates and methanesulfonates. The compound may be dissolved in a base which will be described below or mixed therewith in an amount exceeding its solubility and dispersed therein in a microcrystalline state.

The invention compound is contained in the preparation in an amount of 0.05 to 30% by weight, preferably 0.1 to 20% by weight. When the percutaneously absorbable preparation of the present invention is of adhering type, such as a tape, patch or cataplasm, the compound is contained in the medicated layer of the preparation excluding the support at a proportion as described above. The preparation may be used for plaster tape. When the content of the compound is less than 0.05 wt. %, the percutaneous absorption of the drug will be insufficient to give a blood drug concentration high enough to exhibit its effect with a practical application area (150 cm$^2$ or below). On the other hand, when the content thereof exceeds 30% by weight, the resulting pharmaceutical preparation may cause the base to crack. Therefore, for example, when the preparation is of the adhering type, the applicability thereof will be poor.

The crosslinked polyvinylpyrrolidone to be used in the present invention is prepared by the copolymerization of N-vinyl-2-pyrrolidone with a polyfunctional monomer and is contained in the pharmaceutical preparation in a particulate state. The polyfunctional monomer to be used in the above copolymerization includes di(meth)acrylates such as hexamethylene glycol di(meth)acrylate, ethylene glycol di(meth)acrylate, triethylene glycol di(meth)acrylate, tetraethylene glycol di(meth)acrylate and polyethylene glycol di(meth)acrylate; tri(meth)acrylates such as trimethylolpropane triacrylate; tetra(meth)acrylates such as tetramethylolmethane tetraacrylate; polyallyl compounds such as diethylene glycol bisallyl carbonate, triallylglycerin and triallyl cyanurate; and polymaleimides such as ethylenebismaleimide. Further, the polyfunctional monomer includes cyclic acid amides such as N,N'-divinylimidazolidone, N,N'-divinylhexahydropyrimidinone and N-vinyl-3-ethylidenepyrrolidone; divinylbenzene; N,N'-methylenebisacrylamide; ethylidenebisvinylpyrrolidone; divinyl ketone; butadiene and isoprene. The amount of the polyfunctional comonomer is preferably 0.1 to 20% by weight, still preferably 0.5 to 10% by weight, based on the vinylpyrrolidone monomer used. When the amount of the polyfunctional monomer is less than 0.1% by weight, the resulting crosslinked polyvinylpyrrolidone will dissolve in a base which will be described below, or will be significantly swollen therewith, so that the retention of the particulate structure thereof in the preparation will be difficult. On the other hand, when the amount exceeds 20% by weight, the resulting crosslinked polyvinylpyrrolidone will hardly be swollen with the pharmaceutical preparation, so that the drug-releasing properties of the preparation will hardly be improved.

Alternatively, the crosslinked polyvinylpyrrolidone can be prepared by treating a soluble non-crosslinked polyvinylpyrrolidone with thionyl chloride, phosphorus trichloride or phosphorus pentachloride in an organic solvent under heating.

The crosslinked polyvinylpyrrolidone may be a commercially available one and preferable examples thereof include Kollidon CL ® (a product of BASF) and Polyplasdone XL ® (a product of GAF). The processes for the preparation of these compounds are described in U.S. Pat. Nos. 3,759,880, 3,933,766, 3,689,439, 4,139,688 and 4,180,633.

The crosslinked polyvinylpyrrolidones described above exhibit proper swellability with water. Accordingly, when a pharmaceutical preparation containing one of the crosslinked polyvinylpyrolidones is applied to the skin, the preparation is swollen with moisture such as sweat to enhance the drug-releasing properties thereof. The crosslinked polyvinylpyrrolidone is contained in the pharmaceutical preparation of the present invention at a proportion of 0.5 to 20% by weight. When the percutaneously absorbable preparation is of the adhering type, the crosslinked polyvinylpyrrolidone is contained in the proportion as described above based on the total weight of the medicated layer. When the proportion of the crosslinked polyvinylpyrrolidone is less than 0.5% by weight, the release of the drug will not be accelerated, while when it exceeds 20% by weight, the tackiness of the preparation will be low, particularly when the preparation is in the form of a tape.

The base to be used in the present invention varies depending upon the use of the pharmaceutical preparation. The preparation of the present invention may take a form selected from among tapes, patches, cataplasms, ointments and creams. A percutaneous preparation of an adhering type such as tapes, patches, cataplasms or plasters is prepared by forming a medicated layer on a suitable support. These adhering-type preparations are preferably used in order to control the dose of each application accurately, among which tapes and patches are more preferable from the standpoint of the convenience in application.

The base to be used in the tape or patch according to the present invention is one having a tack strength high enough to fix the preparation to the surface of the skin at ordinary temperatures for a long time. Examples thereof include acrylic, rubber and silicone pressure-sensitive adhesives, among which, acrylic and rubber pressure-sensitive adhesives are preferably used with respect to tack properties and cost.

The acrylic pressure-sensitive adhesive is preferably a polymer or copolymer comprising one or more monomers selected from among alkyl (meth)acrylates prepared from an aliphatic alcohol having 4 to 18 carbon atoms and (meth)acrylic acid, or a copolymer of an alkyl (meth)acrylate as described above with other functional monomers. Examples of the alkyl (meth)acrylate include butyl acrylate, isobutyl acrylate, hexyl acrylate, octyl acrylate, 2-ethylhexyl acrylate, isooctyl acrylate, decyl acrylate, isodecyl acrylate, lauryl acrylate, stearyl acrylate, butyl methacrylate, isobutyl methacrylate, 2-ethylhexyl methacrylate, isooctyl methacrylate, decyl methacrylate, isodecyl methacrylate, lauryl methacrylate and stearyl methacrylate.

The functional monomers usable in the preparation of the above copolymers are classified into hydroxylated monomers, carboxylated monomers and amide monomers. The hydroxylated monomers include 2-hydroxyethyl (meth)acrylate and hydroxypropyl (meth)acrylate. The carboxylated monomers include $\alpha,\beta$-unsaturated carboxylic acids such as acrylic and methacrylic acids; monoalkyl maleates such as butyl maleate; and maleic, fumaric and crotonic acids. Maleic anhydride can also form a copolymer similar to that obtained from maleic acid and thus is usable. The amide monomers include acrylamide; alkyl(meth)acrylamides such as dimethylacrylamide and diethylacrylamide; alkyl ether methylol (meth)acrylamides such as butoxymethylacrylamide and ethoxymethylacrylamide; diacetone acrylamide and vinylpyrrolidone. Further, vinyl acetate, styrene, $\alpha$-methylstyrene, vinyl chloride, acrylonitrile, ethylene, propylene and butadiene may also be used.

The acrylic pressure-sensitive adhesive can be prepared by copolymerizing monomers as described above according to a conventional process. It is preferable that the alkyl (meth)acrylate be contained in an amount of at least 50% by weight based on the whole comonomers.

The rubber pressure-sensitive adhesive includes natural rubber, synthetic isoprene rubber, polyisobutylene, polyvinyl ether, polyurethane, polyisoprene, polybutadiene, styrene-butadiene copolymers, styrene-isoprene copolymers and styrene-isoprene-styrene block copolymers.

The silicone pressure-sensitive adhesive includes silicone rubbers such as polyorganosiloxane.

If necessary, the above pressure-sensitive adhesive may further contain various additives. Examples of the additives include tackifiers such as rosin resin, polyterpene resin, cumarone-indene resin, petroleum resin or terpene-phenol resin; plasticizers such as liquid polybutene, mineral oil, lanolin, liquid isobutylene or liquid polyacrylate; fillers and age resisters.

When the percutaneously absorbable preparation of the present invention is in the form of a cataplasm, the base to be used includes natural polymers such as sodium alginate, gelatin, corn starch and tragacanth gum; cellulose polymers such as methylcellulose, hydroxyethylcellulose and carboxymethylcellulose; starch polymers such as dextrin and carboxymethylstarch; and synthetic polymers such as polyvinyl alcohol, polysodium acrylate, methoxyethylene-maleic anhydride copolymer, polyvinyl ether and polyvinylpyrrolidone. If necessary, the base may contain purified water; a polyhydric alcohol humectant such as glycerin or propylene glycol; an inorganic filler such as kaolin, bentonite, zinc oxide or titanium dioxide; a viscosity modifier; a crosslinking agent and/or an age resister.

When the pharmaceutical preparation is used as an ointment or a cream, the base includes beeswax, fats and oils, white vaseline, paraffin, Plastibase, 50 w (trade name), higher fatty acids, higher alcohols, emulsifiers, macrogols and carboxy vinyl polymers. If necessary, the base may contain a fat-soluble solubilizing agent such as crotamiton, liquid paraffin, isopropyl myristate or diethyl sebacate; purified water; ethanol; a polyhydric alcohol such as glycerol as a water-soluble solubilizing agent and/or a pH regulator.

If necessary, the percutaneously absorbable preparation of the present invention may further contain a suitable absorption accelerator for the purpose of improving the percutaneous absorbability of a drug. Examples of the absorption accelerator include isopropyl myristate, diethyl sebacate, sorbitan monolaurate, glycerol monooleate, sodium oleyl phosphate, sodium lauryl sulfate, octyl phenyl ether, adduct of polyethylene glycol and octyl phenyl ether, lauryl ether, adduct of polyethylene glycol and lauryl ether, sorbitan monooleate, adduct of polyethylene glycol and sorbitan monooleate, lauroyldiethanolamide, lauroylsarcosine, oleoylsarcosine sugar ester, lecithin, glycyrrhetine, urea, salicylic acid, calcium thioglycolate, lactic acid, lactate esters, olive oil, squalene, lanolin, liquid paraffin and glycerin Particularly, lactates of aliphatic alcohols having 12 to 18 carbon atoms are preferable. Examples thereof include myristyl lactate, lauryl lactate and cetyl lactate.

The absorption accelerator is contained in the pharmaceutical preparation in an amount of 10% by weight or below, preferably 0.1 to 10% by weight. When the pharmaceutical preparation is of the adhering type, the accelerator is contained in an amount as described above based on the whole medicated layer. When the proportion of the accelerator exceeds 10% by weight, the resulting preparation will be an irritant to the skin and cause flaring or itching when applied to the skin.

When the percutaneously absorbable preparation of the present invention is in the form of an ointment or a cream, it is prepared by adding the invention compound, a crosslinked polyvinylpyrrolidone and, if necessary, an absorption accelerator to a base as defined above, followed by mixing.

When the percutaneously absorbable preparation of the present invention is of an adhering type, such as tapes, patches or cataplasms, it is prepared by forming a medicated layer comprising the invention compound, a crosslinked polyvinylpyrrolidone, a base and, if necessary, an absorption accelerator on a suitable support. The process for forming such a layer on a support includes various known application processes such as solution coating, hot-melt coating and electron beam curing emulsion coating, among which solution coating is particularly preferable. According to solution coating, an adhering-type preparation can be prepared by diluting a base as described above with a proper solvent, adding the invention compound, a crosslinked polyvinylpyrrolidone and, if necessary, an absorption accelerator and various additives to the diluted base to obtain a dispersion, applying the dispersion to the surface of a support and drying the obtained laminate to remove the solvent. It is also prepared by applying the dispersion to a release sheet or liner, drying the formed layer and transferring the layer to a support. The thickness of the medicated layer thus formed on a support is generally from about 30 $\mu$m to about 200 $\mu$m, though it varies depending upon the use. When the thickness is less than 30 $\mu$m, the resulting adhering-type preparation will not contain a necessary amount of a drug per unit area. Further, when the preparation is in the form of a tape or a patch, no sufficient tackiness will not be attained. On the other hand, when the thickness exceeds 200 $\mu$m, the drug present near the support in the medicated layer will have difficultly in reaching the surface of the skin by diffusion, so the drug contained in the preparation will not be utilized effectively. The medicated layer may be covered with a release sheet in order to protect the layer until service.

The support to be used in the above sticking-type preparation may be any conventional one for adhering-type preparations and examples of the material of the support include cellulose acetate, ethylcellulose, polyethylene terephthalate, plasticized vinyl acetate-vinyl chloride copolymer, nylon, ethylene-vinyl acetate copolymer, plasticized polyvinyl chloride, polyurethane, polyvinylidene chloride and aluminum. These materials may be used either as a single-layer sheet or as a laminate comprising two or more sheets. Alternatively, all of the materials except aluminum may be also used as a woven or nonwoven fabric.

The adhering-type preparation thus prepared is applied to an affected part. When the preparation is a cataplasm, it is fixed to the surface of the skin with an adhesive plaster or the like, since it has poor tackiness.

FUNCTION

The percutaneously absorbable preparation of the present invention is characterized in that the invention compound contained therein can be easily absorbed into the blood through the skin. The mechanism how this advantageous characteristic is brought about is thought to be as follow, though the details thereof are not apparent. Namely, the crosslinked polyvinylpyrrolidone contained in the pharmaceutical preparation is nonswellable with the invention compound but is swellable with water. Therefore, when the pharmaceutical preparation of the present invention is applied to the surface of the skin, the crosslinked polyvinylpyrrolidone absorbs moisture such as sweat and is swollen therewith to function so as to expel the invention compound from the preparation. By virtue of this function of the crosslinked polyvinylpyrrolidone, the invention compound can be effectively released from the preparation and administered into the blood through the skin.

The percutaneously absorbable preparation of the present invention is characterized in that eperisone, tolperisone or a salt thereof can be effectively absorbed percutaneously.

The preparation of the present invention can be used in various forms such as tapes, patches, cataplasms, ointments and creams. Particularly, it is preferably used as an adhering-type preparation such as a tape, patch or cataplasm.

BRIEF DESCRIPTION OF THE DRAWINGS

FIG. 1 is a graph showing the percutaneous absorbability of eperisone hydrochoride with respect to the tapes made in the Examples and Comparative Examples.

FIG. 2 is a graph showing the dissolution rate of eperisone hydrochloride with respect to the tapes made in the Examples and Comparative Examples.

FIG. 3 is a graph showing the percutaneous absorbability of tolperisone hydrochloride with respect to the tapes made in the Examples and Comparative Examples.

EXAMPLE

The present invention will now be described by referring to the following Examples.

Example 1

A copolymer prepared by the copolymerization of 45 parts by weight of 2-ethylhexyl acrylate with 55 parts by weight of 2-ethylhexyl methacrylate was dissolved in ethyl acetate to give a base solution having a solid content of 34% by weight. Four parts by weight of eperisone hydrochloride and 2 parts by weight of Kollidon CL ® (crosslinked polyvinylpyrrolidone, a product of BASF) were added to 100 parts by weight of the base solution and the obtained mixture was thoroughly stirred in a dissolver to give a homogeneous dispersion containing eperisone hydrochloride in a microcrystalline state and Kollidon CL ® in a particulate state. This dispersion was applied to a polyethylene terephthalate release sheet having a thickness of 45 μm and dried in a Geer oven of 65° C. for 25 minutes to form a medicated layer. This layer was transferred to a polyethylene terephthalate film having a thickness of 10 μm to give a tape having a medicated layer containing 10% by weight of eperisone hydrochloride and 5% by weight of Kollidon CL ® and a thickness of 80 μm laminated thereon. Into this medicated layer, Kollidon CL ® in a particulate state and eperisone hydrochloride in a microcrystalline state were dispersed.

The tape thus made was examined for percutaneous absorbability and dissolution rate of a drug according to the following methods.

Percutaneous absorbability of drug: The tape made above was cut into a test piece of 60 cm². This test piece was applied to the back of a Japanese white rabbit shorn with an electric clipper or shaver to determine the change in the drug concentration of the plasma with time. The result is given in FIG. 1 together with those of Examples 2 and 3 and Comparative Examples 1 to 3 which will be described below.

Dissolution rate of drug: The tape was examined for dissolution rate of a drug with equipment as defined in the Dissolution Test Method 2 (paddle method) of The Pharmacopoeia of Japan (eleventh edition). First, the tape was cut into a test piece of 10 cm². The support side of this test piece was fixed to a stainless steel fixing device with a double-coated tape and the release sheet was removed from the medicated layer. The fixing device thus treated was sunk at the bottom of a measuring vessel containing 200 ml of distilled water with the medicated layer of the tape facing upward. The resulting system was allowed to stand for a predetermined period of time while keeping the temperature of the distilled water at 37° C. and the rotational speed of the paddle at 100 rpm. Thereafter, the amount of the drug dissolved in the distilled water was measured to determine the change in the amount of the drug dissolved therein with time. The result is given in FIG. 2 together with those of Examples 2 and 3 and Comparative Examples 1 to 3.

Example 2

100 parts by weight of a styrene-isoprene-styrene block copolymer (a product of Shell, Kraton D1107), 15 parts by weight of polybutene (a product of Nippon Oil Co., Ltd., HV-300), 160 parts by weight of a saturated alicyclic hydrocarbon resin (a product of Arakawa Chemical Industry Co., Ltd., Alcon P-90) and 3 parts by weight of butylhydroxytoluene were added to cyclohexane, followed by mixing. Thus, a base solution having a solid content of 42.5% was obtained. 5 parts by weight of eperisone hydrochloride and 2.5 parts by weight of Polyplasdone XL-10 ® (a product of GAF) were added to 100 parts by weight of the base solution. The obtained mixture was thoroughly stirred in a dissolver to give a homogeneous dispersion containing eperisone hydrochloride in a microcrystalline state and Polyplasdone XL-10 ® in a particulate state. A tape was made from this dispersion in a similar manner to that of Example 1. The obtained tape was a laminate comprising a polyethylene terephthalate film having a thickness of 10 μm and a medicated layer having a thickness of 80 μm. This layer contained 10% by weight of eperisone hydrochloride and 5% by weight of Polyplasdone XL-10 ®. The Polyplasdone XL-10 ® was dispersed in the medicated layer in a particulate state and the eperisone hydrochloride was dispersed therein in a microcrystalline state.

Example 3

A copolymer prepared by the copolymerization of 85 parts by weight of 2-ethylhexyl acrylate with 15 parts by weight of vinylpyrrolidone was dissolved in ethyl acetate to give a base solution having a solid content of 33.2% by weight. 4 parts by weight of eperisone hydrochloride, 2 parts by weight of Kollidon CL ® and 0.8 part by weight of cetyl lactate were added to 100 parts by weight of the base solution. The obtained mixture was thoroughly stirred in a dissolver to give a homogeneous dispersion in which microcrystalline eperisone hydrochloride and particulate Kollidon CL ® were homogeneously dispersed. A tape was made from this dispersion in a similar manner to that of Example 1. The medicated layer of the obtained tape contained 10% by weight of eperisone hydrochloride, 5% by weight of Kollidon CL ® and 2% by weight of cetyl lactate. The Kollidon CL ® was dispersed in a particulate state in the layer and the eperisone hydrochloride was dispersed in a microcrystalline state therein.

Comparative Example 1

A tape was made by the same procedure as that of Example 1 except that no Kollidon CL ® was added. The eperisone hydrochloride content of the medicated layer of the tape was 10.5% by weight. The eperisone hydrochloride was dispersed in the layer in a microcrystalline state.

Comparative Example 2

A tape was made by the same procedure as that of Example 2 except that no Polyplasdone XL-10 ® was added. The eperisone hydrochloride content of the medicated layer of the tape was 10.5% by weight. The eperisone hydrochloride was dispersed in the layer in a microcrystalline state.

Comparative Example 3

A tape was made by the same procedure as that of Example 3 except that no Kollidon CL ® was added. The medicated layer of the obtained tape contained 10.5% by weight of eperisone hydrochloride and 2.1% by weight of cetyl lactate. The eperisone hydrochloride was dispersed in the layer in a microcrystalline state.

Example 4

A tape was made in a similar manner to that of Example 1 except that tolperisone hydrochloride was used instead of eperisone hydrochloride. The medicated layer of the obtained tape contained 10% by weight of tolperisone hydrochloride and 5% by weight of Kollidon CL ®. The Kollidon CL ® was dispersed in the layer in a particulate state and the tolperisone hydrochloride was dispersed therein in a microcrystalline state. The obtained tape was examined for the percutaneous absorbability of a drug in a similar manner to that of Example 1. The result is given in FIG. 3 together with those of Examples 5.and 6 and Comparative Examples 4 to 6 which will be described below.

Example 5

A tape was made in a similar manner to that of Example 2 except that tolperisone hydrochloride was used instead of the eperisone hydrochloride. The medicated layer of the obtained tape contained 10% by weight of tolperisone hydrochloride and 5% by weight of Polyplasdone XL-10 ®. The Polyplasdone XL-10 ® was dispersed in the layer in a particulate state and the tolperisone hydrochloride was dispersed therein in a microcrystalline state.

Example 6

A tape was made in a similar manner to that of Example 3 except that tolperisone hydrochloride was used instead of the eperisone hydrochloride. The medicated layer of the tape contained 10% by weight of tolperisone hydrochloride, 5% by weight of Kollidon CL ® and 2% by weight of cetyl lactate The Kollidon CL ® was dispersed in the layer in a particulate state and the tolperisone hydrochloride was dispersed therein in a microcrystalline state.

Comparative Example 4

A tape was made in a similar manner to that of Example 4 except that no Kollidon CL ® was added. The tolperisone hydrochloride content of the medicated layer of the obtained tape was 10.5% by weight and the eperisone hydrochloride was dispersed in the layer in a microcrystalline state.

Comparative Example 5

A tape was made in a similar manner to that of Example 5 except that no Polyplasdone XL-10 ® was added. The tolperisone hydrochloride content of the medicated layer of the obtained tape was 10.5% by weight and the tolperisone hydrochloride was dispersed in the layer in a microcrystalline state.

Comparative Example 6

A tape was made in a similar manner to that of Example 6 except that no Kollidon CL ® was added. The medicated layer of the obtained tape contained 10.5% by weight of tolperisone hydrochloride and 2.1% by weight of cetyl lactate. The tolperisone hydrochloride was dispersed in the layer in a microcrystalline state.

Example 7

65 parts by weight of white vaseline was heated to 70° C., followed by the addition thereto of 20 parts by weight of purified lanolin, 5 parts by weight of Kollidon CL ® and 10% by weight of eperisone hydrochloride. The obtained mixture was kneaded and cooled to give an ointment according to the present invention.

Example 8

10 parts by weight of eperisone hydrochloride was added to 5 parts by weight of propylene glycol heated to 60° C. to give a mixture wherein part of the eperisone hydrochloride was dissolved in the propylene glycol. A mixture previously prepared by mixing 5 parts by weight of Kollidon CL ® and 3 parts by weight of cetyl lactate with 77 parts by weight of Plastibase (resistered trademark of Squibb Japan Inc.; comprising 95 parts by weight of liquid paraffin and 5 parts by weight of polyethylene having a molecular weight of 10000 to 30000) under heating at 60° C. was added to the above mixture. The resulting mixture was cooled to room temperature under stirring to give an ointment according to the present invention.

Example 9

65 parts by weight of white vaseline was heated to 70° C., followed by the addition thereto of 20 parts by weight of purified lanolin, 5 parts by weight of Kollidon CL ® and 10 parts by weight of tolperisone hydrochloride. The obtained mixture was kneaded and cooled to give an ointment according to the present invention.

Example 10

5 parts by weight of propylene glycol was heated to 60° C., followed by the addition thereto of 10 parts by weight of tolperisone hydrochloride. Thus, a mixture wherein part of the tolperisone hydrochloride was dissolved in the propylene glycol was obtained. A mixture previously prepared by mixing 5 parts by weight of Kollidon CL ® and 3 parts by weight of cetyl lactate with 77 parts by weight of Plastibase under heating at 60° C. was added to the above mixture. The obtained mixture was cooled to room temperature under stirring to give an ointment according to the present invention.

As shown in FIGS. 1 and 2, the tapes of Examples 1 to 3 according to the present invention had excellent percutaneous absorbability of eperisone hydrochloride and the dissolution rate thereof. On the other hand, the tapes of Comparative Examples 1 to 3, containing no crosslinked polyvinylpyrrolidone, were poor in percutaneous absorbability and dissolution rate.

As shown in FIG. 3, the tapes of Examples 4 to 6 according to the present invention are superior to those of Comparative Examples 4 to 6, which do not contain crosslinked polyvinylpyrrolidone, with respect to the percutaneous absorbability of tolperisone hydrochloride and the dissolution rate thereof.

We claim:

1. A pharmacological composition to administer percutaneously, which comprises a pharmacologically effective amount of eperisone, a salt thereof, tolperisone or a salt thereof, a water-swellable crosslinked polyvinylpyrrolidone and a base carrier.

2. The composition as claimed in claim 1, which comprises 0.05 to 30 percent by weight of eperisone, a salt thereof, tolperisone or a salt thereof, 0.5 to 20 percent by weight of the water-swellable crosslinked polyvinylpyrrolidone and a base carrier.

3. The composition as claimed in claim 1, in which said polyvinylpyrrolidone is a copolymer of N-vinyl-2-pyrrolidone and 0.1 to 20 percent by weight, based on the N-vinyl-2-pyrrolidone, of a polyfunctional monomer.

4. The composition as claimed in claim 1, which comprises 0.05 to 30 percent by weight of eperisone, a salt thereof, tolperisone or a salt thereof, 0.5 to 20 percent by weight of the water-swellable crosslinked polyvinylpyrrolidone, a base carrier and up to 10 percent by weight of of a percutaneous absorption enhancer.

5. The composition as claimed in claim 1, in which eperisone, a salt thereof, tolperisone or a salt thereof are present in an amount of not less than their respective saturated solubility and are dispersed in microcrystalline form in the base carrier.

6. The composition as claimed in claim 4, wherein said percutaneous absorption enhancer is present in said composition and is selected from the group consisting of myristyl lactate, lauryl lactate and cetyl lactate.

7. The composition as claimed in claim 1, wherein eperisone hydrochloride is present in said composition.

8. The composition as claimed in claim 1, wherein tolperisone hydrochloride is present in said composition.

* * * * *